(12) United States Patent
Heilman et al.

(10) Patent No.: US 10,112,036 B2
(45) Date of Patent: *Oct. 30, 2018

(54) ENDOVASCULAR CEREBROSPINAL FLUID SHUNT

(71) Applicant: Tufts Medical Center, Inc., Boston, MA (US)

(72) Inventors: Carl Heilman, Wayland, MA (US); Adel M. Malek, Weston, MA (US)

(73) Assignee: Tufts Medical Center, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/920,024

(22) Filed: Oct. 22, 2015

(65) Prior Publication Data

US 2016/0082231 A1 Mar. 24, 2016

Related U.S. Application Data

(60) Continuation of application No. 14/179,622, filed on Feb. 13, 2014, now Pat. No. 9,199,067, which is a (Continued)

(51) Int. Cl.
*A61M 27/00* (2006.01)
*A61M 25/00* (2006.01)

(52) U.S. Cl.
CPC ...... *A61M 27/006* (2013.01); *A61M 25/0075* (2013.01); *A61M 27/002* (2013.01);
(Continued)

(58) Field of Classification Search
CPC ............ A61M 27/006; A61M 27/002; A61M 25/0075; A61M 2025/0076;
(Continued)

(56) References Cited

U.S. PATENT DOCUMENTS

| 3,492,996 A | 2/1970 | Fountain |
| 3,894,541 A | 7/1975 | El-Shafei |

(Continued)

FOREIGN PATENT DOCUMENTS

| EP | 0964636 | 12/1999 |
| EP | 1047341 | 11/2000 |

(Continued)

OTHER PUBLICATIONS

Oh et al., "Implantable Microdevice for the Treatment of Hydrocephalus," Drexel University, Mar. 2011, 155 pages.
(Continued)

*Primary Examiner* — Adam Marcetich
(74) *Attorney, Agent, or Firm* — Occhiuti & Rohlicek LLP

(57) ABSTRACT

An endovascular implantable shunt device for draining cerebrospinal fluid from a patient's subarachnoid space includes a shunt having opposed first and second ends, a one-way valve located at the first end of the shunt, a helical tip disposed at the second end, and a hollow passageway extending between the helical tip and one-way valve. The helical tip is constructed to penetrate a patient's sinus wall. Cerebrospinal fluid drains through the helical tip and out through the valve.

16 Claims, 5 Drawing Sheets

Related U.S. Application Data continuation of application No. 13/569,212, filed on Aug. 8, 2012, now Pat. No. 8,672,871, which is a division of application No. 12/362,152, filed on Jan. 29, 2009, now abandoned.

(52) U.S. Cl.
CPC ............... A61F 2230/0091 (2013.01); A61M 2025/0076 (2013.01); A61M 2202/0464 (2013.01); A61M 2205/0238 (2013.01); A61M 2210/0687 (2013.01); A61M 2210/0693 (2013.01); A61M 2210/12 (2013.01)

(58) Field of Classification Search
CPC .. A61M 2210/0693; A61M 2210/0687; A61M 2210/12; A61M 2202/0464; A61M 2205/0238; A61M 2210/1003; A61F 2230/0091; A61F 2/2493; A61F 2009/00891; A61F 9/00781; A61B 2017/00247; A61B 2018/00392; A61B 2017/1205
See application file for complete search history.

(56) References Cited

U.S. PATENT DOCUMENTS

| | | | |
|---|---|---|---|
| 4,413,985 | A | 11/1983 | Wellner et al. |
| 4,474,569 | A | 10/1984 | Newkirk |
| 4,475,898 | A | 10/1984 | Brodner et al. |
| 4,631,051 | A | 12/1986 | Harris |
| 4,737,153 | A | 8/1988 | Shimamura et al. |
| 4,950,232 | A | 8/1990 | Ruzicka et al. |
| 5,000,731 | A | 3/1991 | Wong et al. |
| 5,137,288 | A | 8/1992 | Starkey et al. |
| 5,160,325 | A | 11/1992 | Nichols et al. |
| 5,193,546 | A | 3/1993 | Shaknovich |
| 5,385,541 | A | 1/1995 | Kirsch et al. |
| 5,405,316 | A | 4/1995 | Magram |
| 5,429,144 | A * | 7/1995 | Wilk ............ A61F 2/06 128/898 |
| 5,496,329 | A | 3/1996 | Reisinger |
| 5,508,824 | A | 4/1996 | Baba |
| 5,551,427 | A | 9/1996 | Altman |
| 5,634,475 | A | 6/1997 | Wolvek |
| 5,725,571 | A | 3/1998 | Imbert et al. |
| 5,746,725 | A | 5/1998 | Shalon et al. |
| 5,755,775 | A | 5/1998 | Trerotola et al. |
| 5,800,520 | A | 9/1998 | Fogarty et al. |
| 5,830,222 | A | 11/1998 | Makower |
| 5,851,199 | A | 12/1998 | Peerless et al. |
| 5,976,131 | A | 11/1999 | Guglielmi et al. |
| 5,984,929 | A | 11/1999 | Bashiri et al. |
| 6,015,405 | A | 1/2000 | Schwartz |
| 6,068,638 | A | 5/2000 | Makower |
| 6,071,292 | A | 6/2000 | Makower et al. |
| 6,093,199 | A | 7/2000 | Brown |
| 6,126,628 | A | 10/2000 | Nissels |
| 6,126,649 | A | 10/2000 | Van Tassel et al. |
| 6,126,672 | A | 10/2000 | Berryman |
| 6,159,225 | A | 12/2000 | Makower |
| 6,186,972 | B1 | 2/2001 | Nelson et al. |
| 6,190,353 | B1 | 2/2001 | Makower et al. |
| 6,231,587 | B1 | 5/2001 | Makower |
| 6,248,112 | B1 * | 6/2001 | Gambale ............ A61B 17/3468 606/108 |
| 6,264,625 | B1 | 7/2001 | Rubenstein et al. |
| 6,283,934 | B1 | 9/2001 | Borgeson |
| 6,283,947 | B1 | 9/2001 | Mirzaee |
| 6,283,951 | B1 | 9/2001 | Flaherty et al. |
| 6,283,983 | B1 | 9/2001 | Makower |
| 6,287,317 | B1 | 9/2001 | Makower et al. |
| 6,302,875 | B1 | 10/2001 | Makower et al. |
| 6,330,884 | B1 | 12/2001 | Kim |
| 6,375,615 | B1 | 4/2002 | Flaherty et al. |
| 6,379,319 | B1 | 4/2002 | Garibotto et al. |
| 6,402,771 | B1 | 6/2002 | Palmer et al. |
| 6,432,127 | B1 | 8/2002 | Kim et al. |
| 6,464,709 | B1 | 10/2002 | Shennib et al. |
| 6,491,707 | B2 | 12/2002 | Makower et al. |
| 6,508,824 | B1 | 1/2003 | Flaherty et al. |
| 6,527,790 | B2 | 3/2003 | Chien et al. |
| 6,544,230 | B1 | 4/2003 | Flaherty et al. |
| 6,561,998 | B1 | 5/2003 | Roth et al. |
| 6,569,145 | B1 | 5/2003 | Shmulewitz et al. |
| 6,575,997 | B1 | 6/2003 | Palmer et al. |
| 6,579,311 | B1 | 6/2003 | Makower |
| 6,589,164 | B1 | 7/2003 | Flaherty |
| 6,602,241 | B2 | 8/2003 | Makower et al. |
| 6,613,081 | B2 | 9/2003 | Kim et al. |
| 6,616,675 | B1 | 9/2003 | Evard et al. |
| 6,638,293 | B1 | 10/2003 | Makower et al. |
| 6,655,386 | B1 | 12/2003 | Makower et al. |
| 6,660,021 | B1 | 12/2003 | Palmer et al. |
| 6,660,024 | B1 | 12/2003 | Flaherty et al. |
| 6,685,648 | B2 | 2/2004 | Flaherty et al. |
| 6,685,716 | B1 | 2/2004 | Flaherty et al. |
| 6,709,444 | B1 | 3/2004 | Makower |
| 6,716,238 | B2 | 4/2004 | Elliott |
| 6,719,750 | B2 | 4/2004 | Varner et al. |
| 6,726,677 | B1 | 4/2004 | Flaherty et al. |
| 6,746,426 | B1 | 6/2004 | Flaherty et al. |
| 6,746,464 | B1 | 6/2004 | Makower |
| 6,863,684 | B2 | 3/2005 | Kim et al. |
| 7,056,325 | B1 | 6/2006 | Makower et al. |
| 7,083,588 | B1 | 8/2006 | Shmulewitz et al. |
| 7,094,230 | B2 | 8/2006 | Flaherty et al. |
| 7,118,549 | B2 | 10/2006 | Chan |
| 7,134,438 | B2 | 11/2006 | Makower et al. |
| 7,141,041 | B2 | 11/2006 | Seward |
| 7,150,737 | B2 | 12/2006 | Purdy et al. |
| 7,172,571 | B2 | 2/2007 | Moskowitz et al. |
| 7,179,270 | B2 | 2/2007 | Makower et al. |
| 7,189,221 | B2 | 3/2007 | Silverberg et al. |
| 7,191,015 | B2 | 3/2007 | Lamson et al. |
| 7,300,458 | B2 | 11/2007 | Henkes et al. |
| 7,303,571 | B2 | 12/2007 | Makower et al. |
| 7,316,655 | B2 | 1/2008 | Garibotto |
| 7,351,247 | B2 | 4/2008 | Kupiecki et al. |
| 7,357,794 | B2 | 4/2008 | Makower et al. |
| 7,407,506 | B2 | 8/2008 | Makower et al. |
| 7,547,294 | B2 | 6/2009 | Seward et al. |
| 7,559,923 | B2 | 7/2009 | Seward et al. |
| 7,606,615 | B2 | 10/2009 | Makower et al. |
| 7,608,064 | B2 | 10/2009 | Putz |
| 7,637,870 | B2 | 12/2009 | Flaherty et al. |
| 7,648,517 | B2 | 1/2010 | Makower et al. |
| 7,670,329 | B2 | 3/2010 | Flaherty et al. |
| 7,691,080 | B2 | 4/2010 | Seward et al. |
| 7,729,738 | B2 | 6/2010 | Flaherty et al. |
| 7,797,053 | B2 | 9/2010 | Atkinson et al. |
| 7,846,172 | B2 | 12/2010 | Makower |
| 7,955,343 | B2 | 6/2011 | Makower et al. |
| 7,966,057 | B2 | 6/2011 | Macaulay et al. |
| 7,989,042 | B2 | 8/2011 | Obara et al. |
| 7,998,103 | B2 | 8/2011 | El Shalei et al. |
| 8,043,247 | B1 | 10/2011 | Glenn |
| 8,075,580 | B2 | 12/2011 | Makower et al. |
| 8,083,708 | B2 | 12/2011 | Flaherty et al. |
| 8,088,140 | B2 | 1/2012 | Ferrera et al. |
| 8,090,430 | B2 | 1/2012 | Makower et al. |
| 8,214,015 | B2 | 7/2012 | Macaulay et al. |
| 8,295,947 | B2 | 10/2012 | Lamson et al. |
| 8,323,305 | B2 | 12/2012 | Epstein et al. |
| 8,366,651 | B2 | 2/2013 | Dakin et al. |
| 8,540,759 | B2 | 9/2013 | Porter |
| 8,585,596 | B1 | 11/2013 | Flaherty et al. |
| 8,672,871 | B2 | 3/2014 | Heilman et al. |
| 8,672,920 | B2 | 3/2014 | Makower et al. |
| 8,727,988 | B2 | 5/2014 | Flaherty et al. |
| 8,740,833 | B2 | 6/2014 | Moskowitz et al. |
| 8,753,366 | B2 | 6/2014 | Makower et al. |
| 8,795,317 | B2 | 8/2014 | Grandfield et al. |

(56) References Cited

U.S. PATENT DOCUMENTS

| | | | |
|---|---|---|---|
| 8,926,680 B2 | 1/2015 | Ferrera et al. | |
| 8,974,513 B2 | 3/2015 | Ford et al. | |
| 9,039,749 B2 | 5/2015 | Shrivastava et al. | |
| 9,168,172 B1 | 10/2015 | Berdahl | |
| 9,387,311 B1 | 7/2016 | Heilman et al. | |
| 9,402,982 B2 | 8/2016 | Baert et al. | |
| 9,433,429 B2 | 9/2016 | Vale et al. | |
| 9,545,505 B2 | 1/2017 | Heilman et al. | |
| 2001/0025643 A1* | 10/2001 | Foley | A61F 2/24 128/898 |
| 2002/0123786 A1* | 9/2002 | Gittings | A61B 17/00234 623/1.11 |
| 2002/0183786 A1 | 12/2002 | Girton | |
| 2002/0188308 A1 | 12/2002 | Tu et al. | |
| 2003/0100943 A1 | 5/2003 | Bolduc | |
| 2003/0125801 A1 | 7/2003 | Yodfat | |
| 2003/0135147 A1 | 7/2003 | Rosenberg et al. | |
| 2003/0181938 A1 | 9/2003 | Roth et al. | |
| 2003/0191520 A1 | 10/2003 | Pelton | |
| 2003/0220604 A1 | 11/2003 | Al-Anazi | |
| 2003/0225395 A1 | 12/2003 | Griffis et al. | |
| 2003/0229366 A1 | 12/2003 | Reggie et al. | |
| 2004/0059280 A1 | 3/2004 | Makower et al. | |
| 2004/0087887 A1 | 5/2004 | Nilsson | |
| 2004/0127843 A1 | 7/2004 | Tu et al. | |
| 2004/0176743 A1 | 9/2004 | Morris et al. | |
| 2004/0186368 A1 | 9/2004 | Ramzipoor et al. | |
| 2004/0236309 A1 | 11/2004 | Yang | |
| 2004/0249439 A1 | 12/2004 | Richter | |
| 2004/0254517 A1 | 12/2004 | Quiroz-Mercado | |
| 2004/0260384 A1 | 12/2004 | Allen | |
| 2005/0096580 A1 | 5/2005 | Moskowitz et al. | |
| 2005/0137646 A1 | 6/2005 | Wallace et al. | |
| 2005/0245906 A1 | 11/2005 | Makower et al. | |
| 2005/0256510 A1 | 11/2005 | Moskowitz et al. | |
| 2005/0281863 A1* | 12/2005 | Anderson | A61K 31/58 424/427 |
| 2006/0004368 A1 | 1/2006 | Zaleski et al. | |
| 2006/0015089 A1 | 1/2006 | Meglin | |
| 2006/0015152 A1 | 1/2006 | Wallace | |
| 2006/0079915 A1 | 4/2006 | Chin | |
| 2006/0173440 A1 | 8/2006 | Lamson et al. | |
| 2006/0224101 A1 | 10/2006 | Glenn | |
| 2007/0112291 A1 | 5/2007 | Borgesen | |
| 2007/0129746 A1 | 6/2007 | Mische | |
| 2007/0156218 A1 | 7/2007 | Williams | |
| 2007/0179426 A1 | 8/2007 | Selden | |
| 2007/0179428 A1 | 8/2007 | Kralick et al. | |
| 2007/0225794 A1 | 9/2007 | Thramann | |
| 2007/0276316 A1 | 11/2007 | Haffner et al. | |
| 2008/0057106 A1 | 3/2008 | Erickson et al. | |
| 2008/0058759 A1 | 3/2008 | Makower et al. | |
| 2008/0097398 A1 | 4/2008 | Mitelberg et al. | |
| 2008/0125805 A1 | 5/2008 | Mische | |
| 2008/0249458 A1 | 10/2008 | Yamasaki | |
| 2009/0005645 A1 | 1/2009 | Frassica et al. | |
| 2009/0017098 A1 | 1/2009 | Di Bartolomeo | |
| 2009/0076357 A1 | 3/2009 | Purdy | |
| 2009/0163847 A1* | 6/2009 | Kapadia | A61F 2/06 604/8 |
| 2009/0227933 A1* | 9/2009 | Karageozian | A61F 9/0017 604/8 |
| 2009/0287291 A1 | 11/2009 | Becking | |
| 2010/0010476 A1 | 1/2010 | Galdonik et al. | |
| 2010/0016887 A1 | 1/2010 | Inderbitzi | |
| 2010/0063531 A1 | 3/2010 | Rudakov | |
| 2010/0076404 A1 | 3/2010 | Ring | |
| 2010/0121357 A1 | 5/2010 | Flaherty et al. | |
| 2010/0191168 A1 | 7/2010 | Heilman | |
| 2010/0222732 A1 | 9/2010 | Sevrain | |
| 2011/0082385 A1 | 4/2011 | Diaz et al. | |
| 2011/0319917 A1 | 12/2011 | Ferrera et al. | |
| 2012/0130467 A1 | 5/2012 | Selden et al. | |
| 2012/0130468 A1 | 5/2012 | Khosravi | |
| 2012/0165757 A1 | 6/2012 | Purdy | |
| 2013/0178828 A1 | 7/2013 | Takagi et al. | |
| 2013/0274646 A1 | 10/2013 | Paris et al. | |
| 2014/0005586 A1 | 1/2014 | Feinstein | |
| 2014/0052160 A1 | 2/2014 | Singh | |
| 2014/0180098 A1 | 6/2014 | Flaherty et al. | |
| 2014/0180222 A1 | 6/2014 | Flaherty et al. | |
| 2014/0207044 A1 | 7/2014 | Baert et al. | |
| 2014/0236207 A1 | 8/2014 | Makower et al. | |
| 2014/0276342 A1 | 9/2014 | Stone | |
| 2014/0277079 A1 | 9/2014 | Vale et al. | |
| 2014/0288414 A1 | 9/2014 | Makower et al. | |
| 2014/0336559 A1 | 11/2014 | Heilman et al. | |
| 2015/0196741 A1 | 7/2015 | Heilman et al. | |
| 2015/0201303 A1 | 7/2015 | Ji et al. | |
| 2015/0209058 A1 | 7/2015 | Ferrera et al. | |
| 2015/0258260 A1 | 9/2015 | Tuseth | |

FOREIGN PATENT DOCUMENTS

| | | |
|---|---|---|
| EP | 1067869 | 1/2001 |
| EP | 1067874 | 1/2001 |
| EP | 1082070 | 3/2001 |
| EP | 1171183 | 1/2002 |
| EP | 1253859 | 11/2002 |
| EP | 1359967 | 11/2003 |
| EP | 1377335 | 1/2004 |
| EP | 1491232 | 12/2004 |
| EP | 1496956 | 1/2005 |
| EP | 1854499 | 11/2007 |
| EP | 2589344 | 5/2013 |
| EP | 1981413 | 11/2014 |
| GB | 2089215 | 6/1982 |
| WO | 1998/016161 | 4/1998 |
| WO | 2002/022028 | 3/2002 |
| WO | 2006/080113 | 8/2006 |
| WO | 2007115314 | 10/2007 |
| WO | 2009/014723 | 1/2009 |
| WO | 20090036039 | 3/2009 |
| WO | 2009/088783 | 7/2009 |
| WO | 20090126935 | 10/2009 |
| WO | 20110011787 | 1/2011 |
| WO | 2012158152 | 11/2012 |
| WO | 2013/034602 | 3/2013 |
| WO | 2015/108917 | 7/2015 |
| WO | 2016070147 | 5/2016 |

OTHER PUBLICATIONS

PCT Notification of Transmittal of the International Search Report and Written Opinion, dated Feb. 17, 2016, for PCT/US2015/058505, Applicant CereVasc, LLC., international filing date Oct. 30, 2015 (16 pages).

Toma et al., Ventriculosinus Shunt, Neurosurg Review, dated Feb. 23, 2010, 7 pages.

Weiner et al., "Current Treatment of Normal-Pressure Hydrocephalus: Comparison of Flow-Regulated and Differential-Pressure Shunt Valves", Neurosurgery vol. 37(5), dated Nov. 1995,13 pages.

Final Office Action for U.S. Appl. No. 12/362,152, dated Mar. 8, 2012 (11 pages).

Non-Final Office Action for U.S. Appl. No. 12/362,152, dated Aug. 5, 2011 (10 pages).

PCT International Search Report and Written Opinion for International Application No. PCT/US2015/011317, Applicant Tufts Medical Center Inc., Forms PCT/ISA/210, 220, and 237, dated Mar. 26, 2015 (15 pages).

PCT International Search Report and Written Opinion for International Application No. PCT/US2016/069280, Applicant CEREVAS LLC, Forms PCT/ISA/210 and 220, dated Mar. 27, 2017 (8 pages).

U.S. Appl. No. 13/569,212, filed Aug. 8, 2012, Endovascular Cerebrospinal Fluid Shunt.

U.S. Appl. No. 14/179,622, filed Feb. 13, 2014, Endovascular Cerebrospinal Fluid Shunt.

U.S. Appl. No. 14/596,335, filed Jan. 14, 2015, Endovascular Cerebrospinal Fluid Shunt.

(56) References Cited

OTHER PUBLICATIONS

U.S. Appl. No. 15/294,000, filed Oct. 14, 2016, Endovascular Cerebrospinal Fluid Shunt.
U.S. Appl. No. 15/480,543, filed Apr. 6, 2017, Endovascular Cerebrospinal Fluid Shunt.
Non-Final Office Action for U.S. Appl. No. 14/179,622, dated May 13, 2015 (13 pages).
Non-Final Office Action for U.S. Appln. No. 14/596,335, dated Jul. 7, 2016 (16 pages)
Non-Final Office Action for U.S. Appln. No. 15/294,000, dated Feb. 16, 2017 (26 pages).
Final Office Action for U.S. Appln. No. 14/596,335, dated Oct. 26, 2016 (18 pages).
PCT International Search Report and Written Opinion for International Appln. No. PCT/US2017/056227, Applicant Cerevasc, LLC, Forms PCT/ISA/210, 220, and 237, dated Mar. 29, 2018 (24 pages).
Annex to Form PCT/IS/2016 Communication Relating to the Results of the Partial International Search for International Application No. PCT/US2018/020667 issued by the International Searching Authority, the European Patent Office, dated May 29, 2018, 2 pages.

* cited by examiner

ENDOVASCULAR CEREBROSPINAL FLUID SHUNT

CROSS-REFERENCE TO RELATED APPLICATIONS

This application is a continuation of U.S. patent application Ser. No. 14/179,622 filed on Feb. 13, 2014 which is a continuation of U.S. patent application Ser. No. 13/569,212 filed on Aug. 8, 2012, which issued as U.S. Pat. No. 8,672,871 on Mar. 18, 2014, which is a divisional of U.S. patent application Ser. No. 12/362,152 filed on Jan. 29, 2009, the contents of which are incorporated herein by reference in its entirety.

BACKGROUND OF THE INVENTION

Field of the Invention

The present invention relates to an endovascular shunt implantable into the wall of a patient's sigmoid sinus, and more particularly, to a shunt capable of draining cerebrospinal fluid from the patient's subarachnoid space to the venous system.

Description of the Related Art

It is known to treat hydrocephalus by draining cerebrospinal fluid (CFS) from the brain with a drain tube, catheter or shunt. See U.S. Pat. Nos. 5,385,541 and 4,950,232. These known devices are complex and invasive. The risk for infection is also increased due to the complexity of these devices.

The known shunts are limited to areas of placement due to fluid flow control. Moreover, the known shunts and methods of placements do not work in conjunction with a body's natural disease control processes. Accordingly, in recent years exploration of placement of a catheter or shunt in the venous sinus of a patient has been explored. See U.S. Pat. No. 6,283,934 and Published Application No. 2005/0256510.

However, fluid flow still poses difficulties due to the complexity of the devices and the placement areas. Commonly, the shunts/catheters are placed through the skull of the patient requiring pressure control to facilitate CSF flow and also creating a dangerous infection site.

Thus, there is a need for an endovascular shunt that can be inserted into the venous system percutaneously.

SUMMARY OF THE INVENTION

The present invention relates to an endovascular CSF shunt that drains CSF from the cistern around the cerebellum into the sigmoid sinus lumen.

The present invention also relates to a method of draining CSF by inserting, deploying and detaching the shunt of the present invention by an endovascular route through the venous system. The venous system is accessed either through the femoral vein or the jugular vein percutaneously.

The endovascular cerebrospinal fluid shunt of the present invention is an improvement over the standard cerebrospinal fluid shunts because it can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

One aspect of the present invention is to provide an implantable shunt device for draining fluid from a patient's subarachnoid space. The device includes a shunt having opposed first and second ends. A one-way valve is located at the first end of the shunt and a helical tip is disposed at the second end. The helical tip penetrates the sigmoid sinus wall of the patient and a hollow passageway extending between the helical tip and the CSF cistern allows the CSF to be drained through the helical tip and out through the valve.

Another aspect of the present invention provides a method for draining cerebrospinal fluid from a patient's subarachnoid space, the method includes the steps of providing a shunt having opposed first and second ends, delivering the shunt to the sinus wall, implanting the helical tip in the sinus wall of the patient; and draining cerebrospinal fluid from the patient.

These and other features, aspects, and advantages of the present invention will become more apparent from the following detailed description of the preferred embodiment relative to the accompanied drawings, in which:

DETAILED DESCRIPTION OF THE PREFERRED EMBODIMENT

Figure 1:
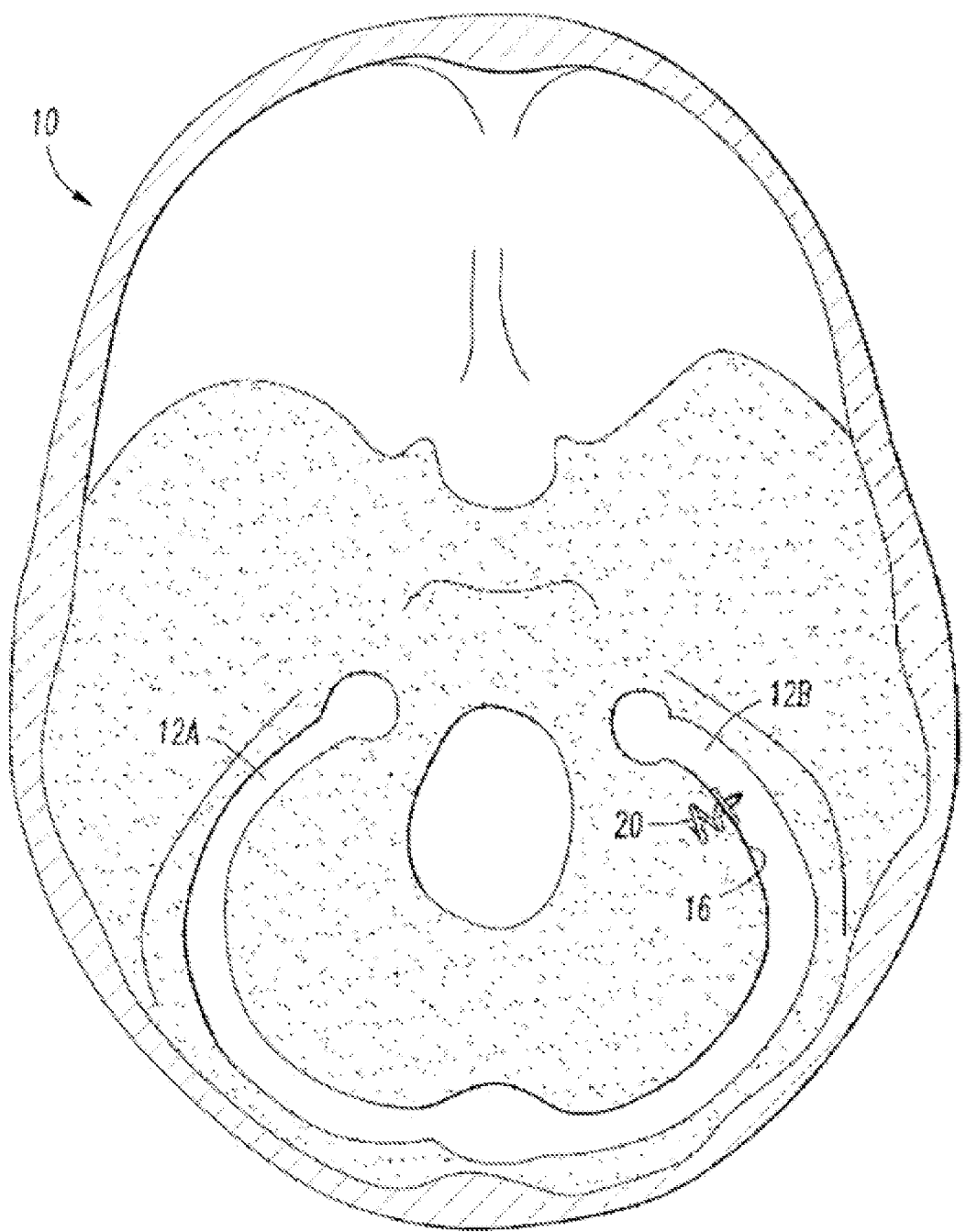
FIG. 1 is a top cross-sectional view of a human skull illustrating the placement of the shunt of the present invention.

Referring to FIG. 1, the endovascular shunt device of the present invention can be delivered to the right or left sigmoid sinus 12A, 12B of a patient's skull 10 via either the right or left jugular vein respectively of the venous system. The sigmoid sinus lumen 12 is located between the temporal bone (FIGS. 3-5) and the cerebellum.

A shunt 20 is implanted into a sigmoid sinus wall 16, so that one end communicates with CSF located in the cistern or CSF space 18 around the cerebellum 19. The device of the present invention uses the body's natural disease control mechanisms by delivering the CSF from cistern 18 into sigmoid sinus lumen 12 of the venous system. The venous system of the patient can be accesses either through the femoral or jugular veins (not shown) percutaneously. It should be appreciated that the shunt device of the present invention can be delivered to the sigmoid sinus via other locations.

Figure 2:
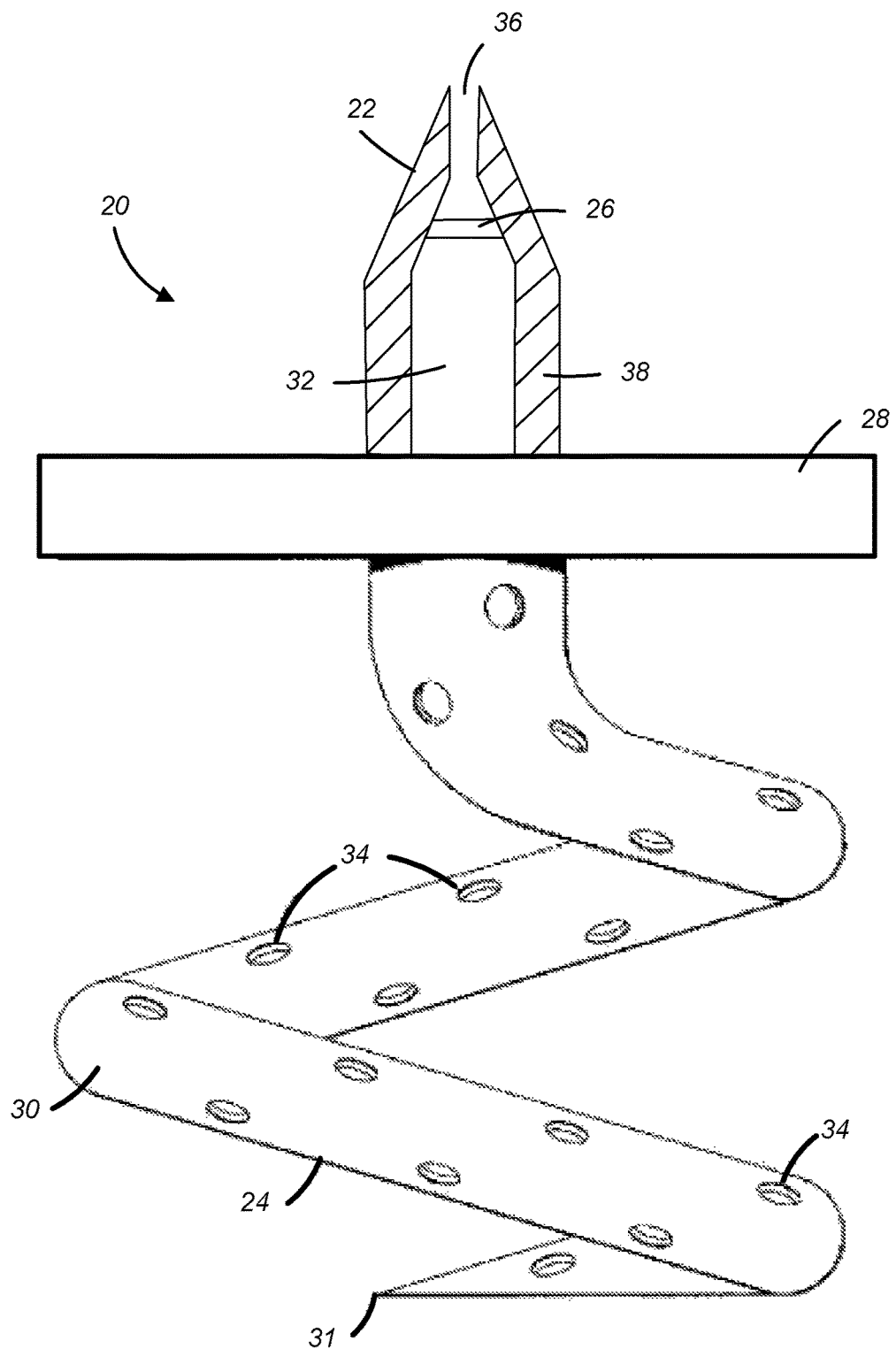
FIG. 2 is a partial cross-section of an embodiment of the endovascular shunt of the present invention.

As shown in FIG. 2, one embodiment of the endovascular CSF shunt 20 of the present invention includes opposed first and second ends 22, 24. A one-way valve 26 is located at first end 22. As will be described further herein, CSF can travel through shunt 20 and out end 22, however, other fluid cannot enter the shunt from open end 22.

A helical tip 30 is located at second end 24. As will be described further herein, helical tip 30 has a closed sharpened end 31 that is adapted to penetrate sinus wall 16. Tip 30 includes a plurality of apertures 34 through which the CSF enters the tip. A hollow passageway 32 extends from tip 30 and open end 22, such that the CSF fluid entering through apertures 34 can pass through valve 26 and pass from an outlet 36.

Figure 3:
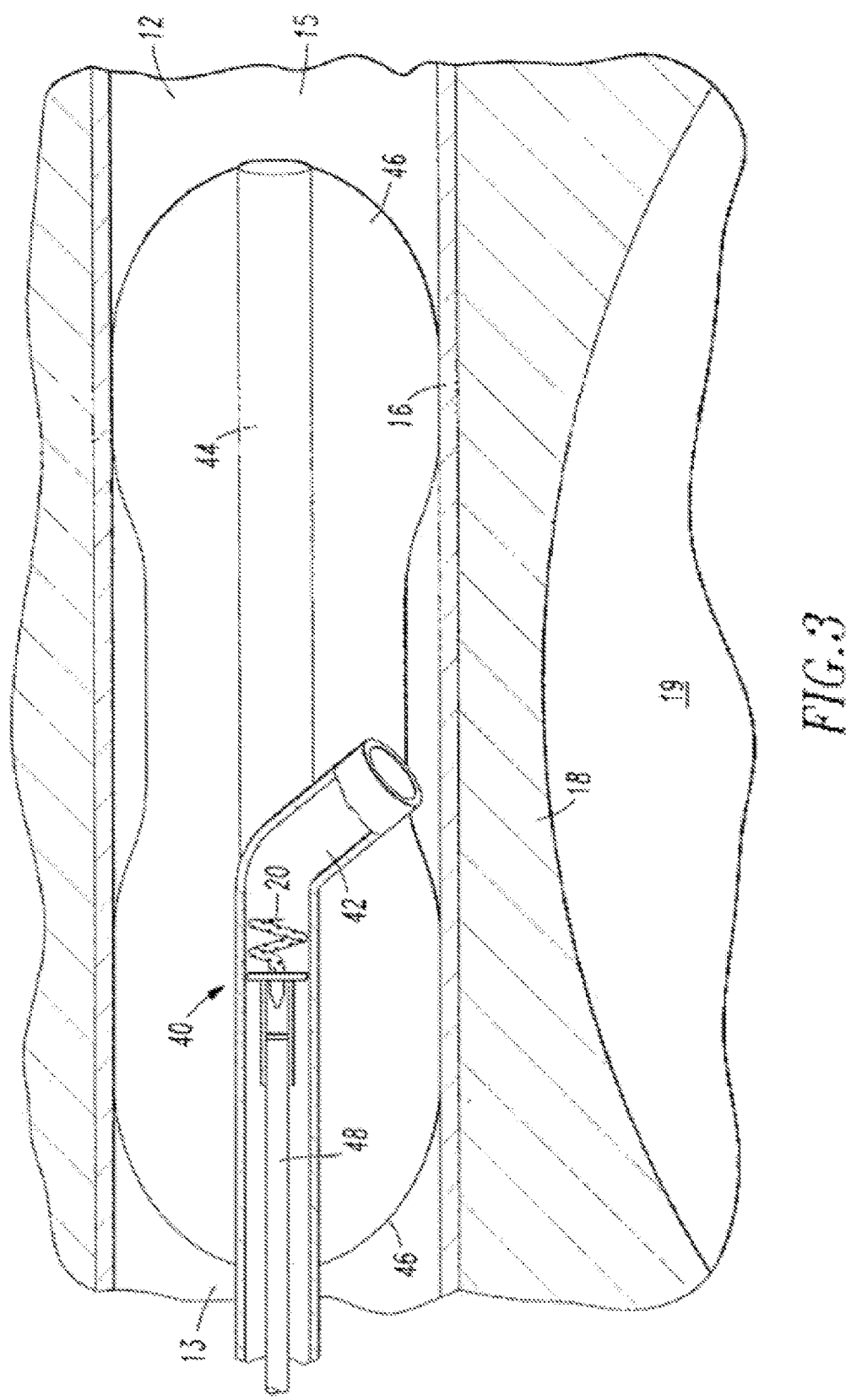
FIG. 3 is a partial view of delivering the endovascular shunt of the present invention to the CSF space of a patient's venous system.
Figure 4:
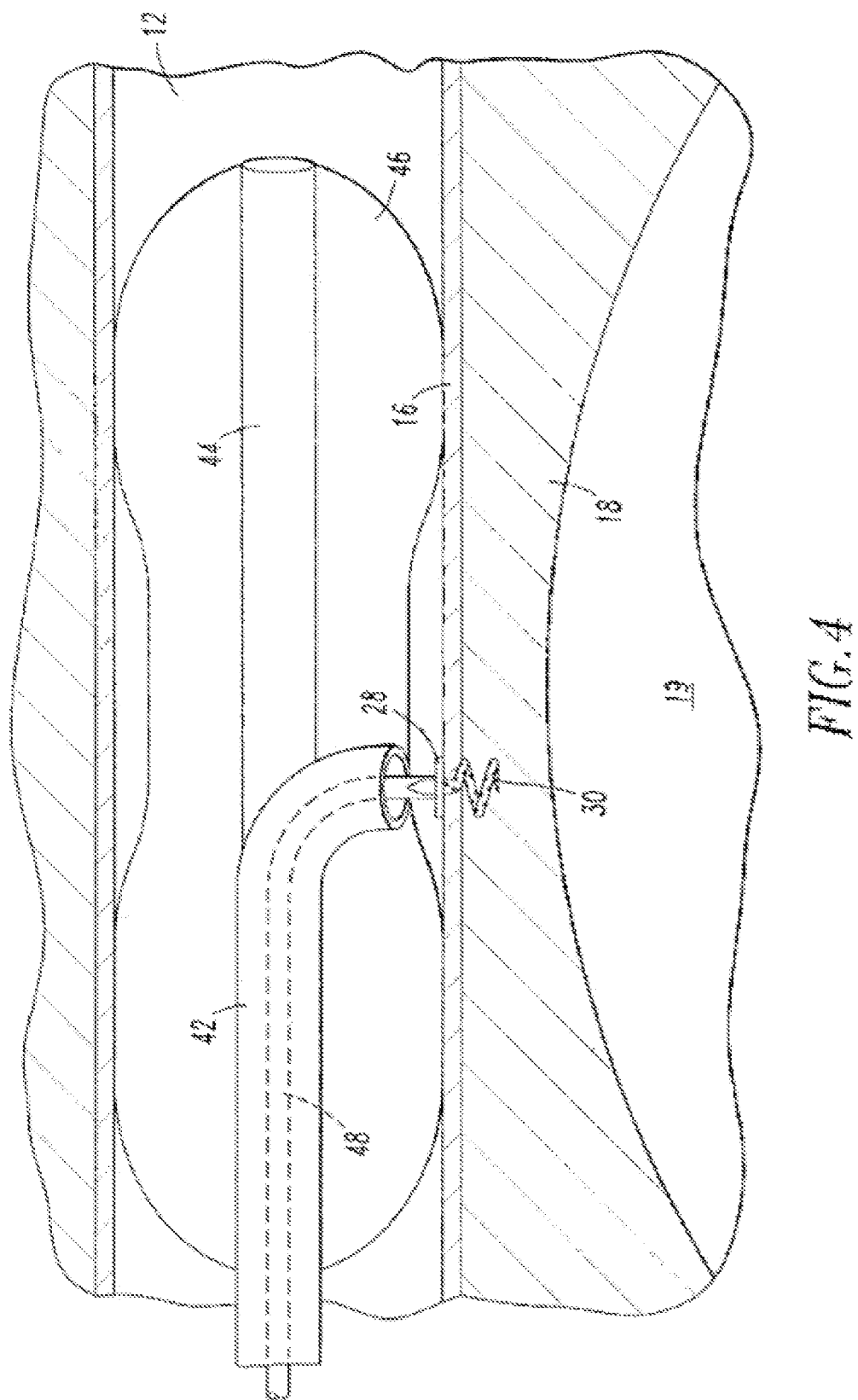
FIG. 4 is a partial view of the implantation of the endovascular shunt of the present invention into the sigmoid sinus wall.
Figure 5:
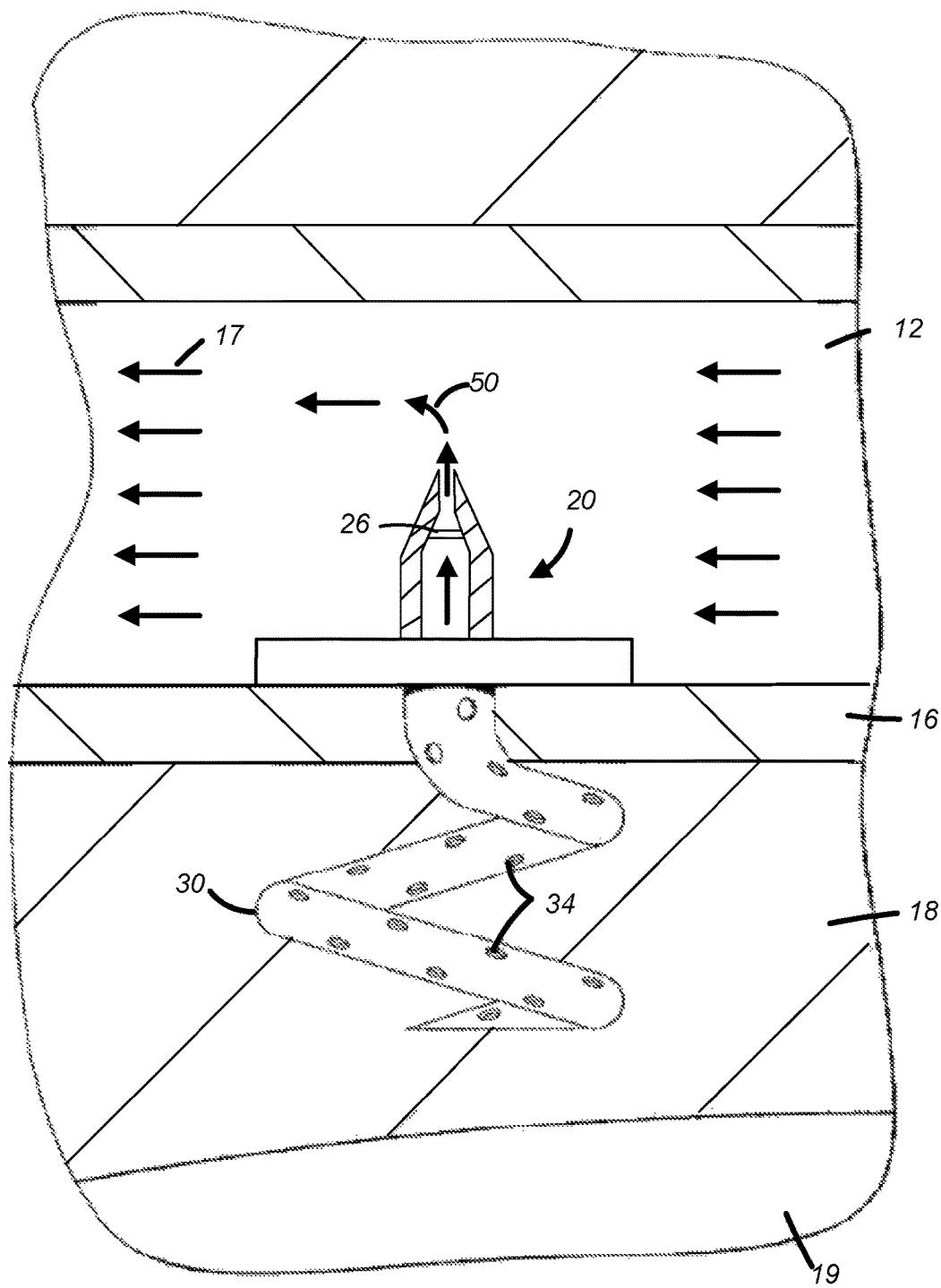
FIG. 5 is a partial view of the endovascular shunt of the present invention implanted in the sigmoid sinus wall.

Referring to FIGS. 3-5 and as described above, a delivery catheter 40 is delivered to the venous system via the femoral or jugular vein. Catheter 40 is inserted into sigmoid sinus lumen 12 at a proximal location 13 toward the neck and inserted toward a distal end 15, which is toward the brain.

Delivery catheter 40 includes a second lumen 44 and a shunt delivery port 42. Lumen 44 directs the entire catheter to the correct location with for example, a guide wire, to allow injection of intravenous contrast to visualize the venous lumen. Lumen 44 also supports balloons 46 that can be deployed to occlude venous flow during stunt implantation. Shunt 20 is positioned at an end of an internal catheter 48 that is manipulated through catheter 40 and port 42. To prevent thrombosis within the sigmoid sinus and around the endovascular shunt, shunt 20 can be provided with an antithrombic coating 38

As shown in FIG. 4, internal catheter 48 facilitates twisting of shunt 20 so that it penetrates through sigmoid sinus wall 12. Catheter 48 includes a hollow lumen to allow CSF withdrawal after shunt penetration of the sigmoid sinus wall to confirm that CSF is flowing through the shunt. However, it must be rigid enough to allow twisting of the shunt such that it penetrates the sigmoid sinus wall. Upon insertion, helical tip 30 extends into cistern 18 and CSF located therein. A projection 28 located on shunt 20 between the ends abuts the wall and prevents the shunt from passing therethrough. Upon placement, internal catheter 48 is detached. The CSF can also be aspirated back prior to detachment of catheter 48.

Thereafter, delivery catheter 40 can be removed and shunt 20 is implanted as shown in FIG. 5. CSF 50 draining from outlet 36 from CSF space 18 is delivered to the venous blood flow 17 and removed. It should be appreciated that other means of fluid removal can communicate with shunt 20 to direct the CSF as desired. It also should be appreciated that shunt 20 can incorporate different tips at end 24.

Thus, the endovascular cerebrospinal fluid shunt of the present invention can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A method for draining cerebrospinal fluid from a patient's subarachnoid space, the method comprising the steps of:

providing an implantable shunt having opposed first and second ends, a one-way valve located at the first end of the shunt, and a tip disposed at the second end, said tip being constructed to penetrate a sinus wall of the patient, wherein the first and second ends are in fluid communication to enable the cerebrospinal fluid (CSF) to be drained through the tip and out through the valve;

endovascularly delivering the shunt to the sinus wall;

penetrating the sinus wall and implanting the second end of the shunt in a CSF space of the patient; and draining cerebrospinal fluid from the patient.

2. The method of claim 1, further comprising providing a plurality of apertures to the tip, the plurality of apertures configured to allow cerebrospinal fluid to enter the tip.

3. The method of claim 1, further comprising providing an antithrombic coating on the shunt.

4. The method of claim 1, wherein endovascularly delivering the shunt to the sinus wall includes delivering percutaneously and implanting the shunt into the sinus wall via a delivery catheter.

5. The method of claim 4, wherein endovascularly delivering the shunt to the sinus wall includes delivering percutaneously and implanting the shunt into the sinus wall via a jugular vein.

6. The method of claim 4, wherein endovascularly delivering the shunt to the sinus wall includes delivering percutaneously and implanting the shunt into the sinus wall via a femoral vein.

7. The method of claim 4, wherein endovascularly delivering the shunt to the sinus wall includes delivering the shunt via a sigmoid sinus lumen.

8. The method of claim 4, further comprising
positioning the shunt at an end of an internal catheter; and
manipulating the internal catheter through the delivery catheter to deliver the shunt to the sinus wall.

9. The method of claim 8, further comprising providing a hollow lumen to the internal catheter.

10. The method of claim 8, further comprising confirming flow of cerebrospinal fluid through the shunt including, after manipulating the internal catheter through the delivery catheter to deliver the shunt to the sinus wall, aspirating the cerebrospinal fluid through the hollow lumen of the internal catheter via the shunt.

11. The method of claim 1, further comprising providing a closed sharpened end to the tip.

12. The method of claim 1, further comprising providing the tip with a formed helix.

13. The method of claim 12, wherein the formed helix has a constant radius.

14. The method of claim 1 further comprising providing a taper to the first end of the shunt.

15. The method of claim 1, further comprising providing a projection between said first and second end of the shunt, wherein said projection extends along a plane perpendicular to a line extending between said first and second ends of said shunt.

16. The method of claim 1, wherein configuring the one-way valve to block liquid from flowing from said first end toward said second end and to permit liquid from flowing from said second end toward said first end.

* * * * *